(12) United States Patent
Dudziak

(10) Patent No.: US 10,105,251 B2
(45) Date of Patent: Oct. 23, 2018

(54) FLEXIBLE SUPPORT BRACE

(71) Applicant: Chris Dudziak, San Francisco, CA (US)

(72) Inventor: Chris Dudziak, San Francisco, CA (US)

( * ) Notice: Subject to any disclaimer, the term of this patent is extended or adjusted under 35 U.S.C. 154(b) by 320 days.

(21) Appl. No.: 14/440,004

(22) PCT Filed: Dec. 13, 2013

(86) PCT No.: PCT/US2013/075066
§ 371 (c)(1),
(2) Date: Apr. 30, 2015

(87) PCT Pub. No.: WO2014/093851
PCT Pub. Date: Jun. 19, 2014

(65) Prior Publication Data
US 2015/0290011 A1 Oct. 15, 2015

Related U.S. Application Data

(60) Provisional application No. 61/737,659, filed on Dec. 14, 2012.

(51) Int. Cl.
*A61F 5/01* (2006.01)
(52) U.S. Cl.
CPC .......... *A61F 5/0109* (2013.01); *A61F 5/0106* (2013.01); *A61F 5/0111* (2013.01); *A61F 5/0118* (2013.01); *A61F 2005/0179* (2013.01)
(58) Field of Classification Search
CPC ........ A61F 5/01; A61F 5/0102; A61F 5/0106; A61F 5/0109; A61F 5/0111; A61F 5/0118
USPC ................ 602/14, 20, 21, 23, 26, 27, 60–65
See application file for complete search history.

(56) References Cited

U.S. PATENT DOCUMENTS

| | | | |
|---|---|---|---|
| 5,134,992 A | 8/1992 | Campbell | |
| 5,498,234 A | 3/1996 | Martel et al. | |
| 5,579,949 A | 12/1996 | Dykes et al. | |
| 5,836,902 A | 11/1998 | Gray | |
| 5,925,010 A | 7/1999 | Caprio, Jr. | |
| 6,520,926 B2 | 2/2003 | Hall | |
| 6,726,641 B2 | 4/2004 | Chiang et al. | |
| 7,018,351 B1 | 3/2006 | Iglesias et al. | |
| 7,517,331 B2 | 4/2009 | Reinhardt et al. | |
| 7,615,021 B2 | 11/2009 | Nordt, III et al. | |
| 7,959,592 B2 * | 6/2011 | Weinberg | A61F 7/02 602/20 |

(Continued)

OTHER PUBLICATIONS

PCT International Search Report, dated Feb. 27, 2014 related to PCT/US13/75066 filed Dec. 13, 2013.

(Continued)

*Primary Examiner* — Keri J Nelson
(74) *Attorney, Agent, or Firm* — Dergosits & Noah LLP

(57) ABSTRACT

A flexible joint brace. The brace has a generally annular structure with a main section and at least one support section aligned along a plane of motion for the human limb or aligned along a meridian proximate to the joint. The main section is formed with larger holes throughout and the support section is formed with smaller holes, the smaller holes providing an increased volume of material that supports and stabilizes the underlying joint in the direction of movement affected by the injury or arthritis.

13 Claims, 11 Drawing Sheets

(56) References Cited

U.S. PATENT DOCUMENTS

| | | |
|---|---|---|
| 8,070,703 B2 | 12/2011 | Skahan et al. |
| 2007/0021706 A1 | 1/2007 | Braunstein et al. |
| 2010/0036300 A1 | 2/2010 | Sheehan et al. |

OTHER PUBLICATIONS

PCT Written Opinion of the International Searching Authority, dated Feb. 27, 2014 related to PCT/US13/75066 filed Dec. 13, 2013.

\* cited by examiner

FLEXIBLE SUPPORT BRACE

TECHNICAL FIELD

This disclosure relates generally to a flexible support brace for therapeutic support and resistance to movement in joints, such as the knee, ankle, wrist and elbow.

BACKGROUND

Joint injuries are common for both competitive and recreational athletes, or for those suffering from arthritis. For example, a sprain is a stretching or tearing of a ligament that joins one bone to another, and may be caused by a fall, twist or blow to the joint, while a strain is a twist, pull or tear of a muscle or tendon (tendons connect muscle to bone) caused by stretching or contracting the muscle or tendon more than normal. Other types of injuries, such as bursitis, tendonitis, or repetitive injuries (carpal tunnel syndrome), may be mild or severe.

While the knee is probably the most commonly injured joint, the ankle, wrist and elbow are also frequently injured. Taking steps to prevent injury is important, but once a joint injury has occurred, keeping the joint stable is the primary goal for rehabilitation. To that end, there are a number of commercial products that seek to provide support. For example, the Ace® bandage is a well-known elastic wrap that is used to wrap around an injured joint, providing some degree of uniform support throughout the injured area. However, such a bandage does not provide focused support and/or resistance to movement based on the nature of the injury or the particular joint movement.

There are also elastic braces sold by Ace and others specifically designed for the ankle, knee, elbow or wrist, for example. However, these location-specific braces are uniform in material construction, and still do not provide adequate focused support and/or resistance to joint movement based on the nature of the injury or the particular joint movement.

Thus, it would thus be desirable to have an improved brace that is focused on providing support and/or resistance to specific joint movements.

DETAILED DESCRIPTION

1. Overview

This disclosure describes a flexible brace for stabilizing and supporting an underlying joint. The brace is formed from a flexible elastic material such as a silicone or polyurethane. The brace has a generally annular structure with a main section formed with a pattern of large holes disposed throughout the main section, and at least one support section formed with a pattern of small holes aligned along a plane of motion of the underlying joint or a meridian proximate to the joint. The smaller holes provide an increased volume of material that supports and stabilizes the underlying joint.

2. Joints and Myofascial Meridians

The human body may be considered an ordered collection of many bones, some connected by joints that permit bodily movement, such as knee, ankle, elbow and wrist, which are the initial focus of embodiments of the braces described herein. Of course, there are connective tissues such as ligaments, synovial fluid, etc., that facilitate joint operation. The concept of myofascial meridians is used to describe lines connective tissue that run throughout the body, linking all parts of the body, and providing the organized structural forces required for motion. (See, e.g., Myers, T., "Anatomy Trains," Journal Of Bodywork and Movement Therapies, vol. 1, issue 2, pp. 91-101, January 1997). All of the foregoing can be taken into account, as further discussed below, in constructing a suitable brace to provide support for different physical issues of the user.

Figure 1:
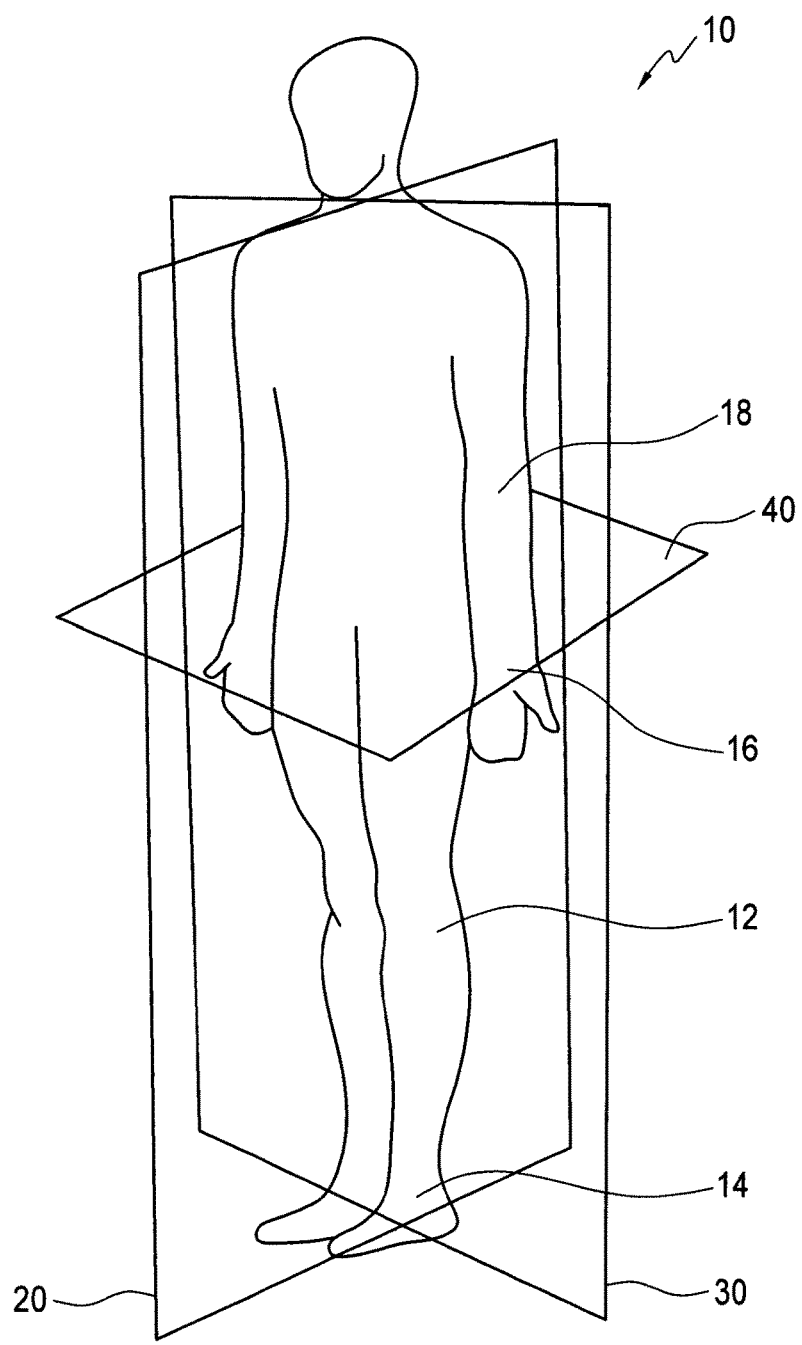
FIG. 1 is a schematic diagram of a human anatomical subject illustrating the three primary planes of joint movement.

It is helpful to provide a frame of reference for physical descriptions, and thus FIG. 1 illustrates an anatomical FIG. 10 having a knee 12, ankle 14, wrist 16 and elbow 18. The three primary planes of movement can be described as: the sagittal plane 20, a vertical plane that divides the body into left half and right half; the frontal plane 22, a vertical plane perpendicular to the sagittal plane that divides the body into an anterior or ventral (front) half and a posterior or dorsal (rear) half; and the transverse plane 24, a horizontal plane that divides the body into upper and lower portions.

The most common joint movement is flexion and extension in the sagittal plane, typified by the hinge joint of the elbow, the modified hinge joint of the knee, and the condyloid joint of the wrist. The movement of the ankle hinge joint is a little more complex, including dorsiflexion (movement is the frontal plane); plantar flexion (movement in the sagittal plane); and a slight circumduction (movement in the transverse plane). Generally, the extensor muscles that create/assist the extension movement are weak compared to those that create/assist the flexion movement.

3. Building a Support Brace, Generally

Figure 2A:
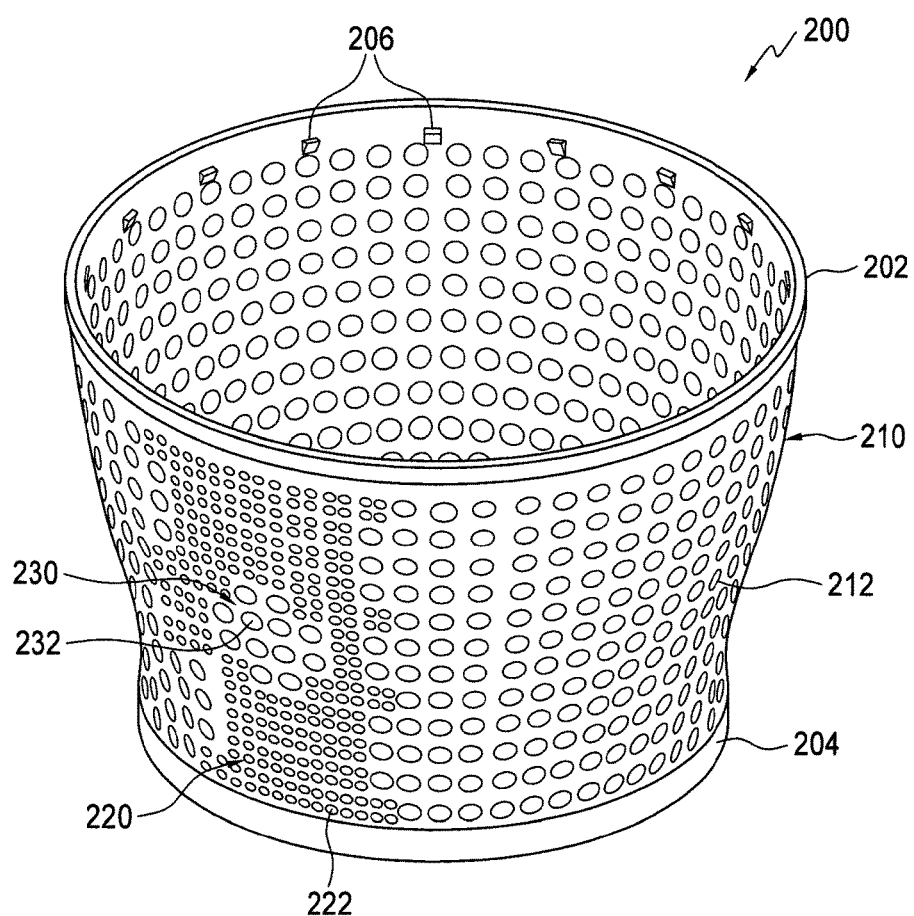
FIG. 2A is a front perspective view of a generic brace structure.
Figure 2B:
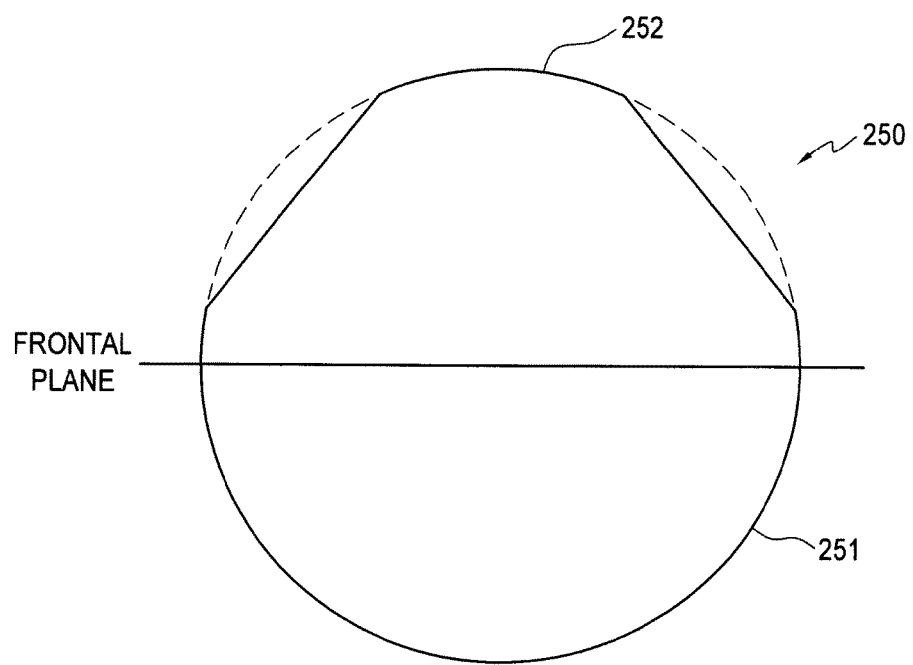
FIG. 2B is a top plan view of an alternative brace structure having one side formed in a trapezoidal shape.

FIG. 2A illustrates one embodiment of an annular structure 200 formed as a flexible brace. The brace 200 can be formed by injection molding, for example, using a silicone material such as Mold Star® silicone rubber or other suitable elastic materials. Although brace 200 is shown as cylindrical in shape, other embodiments can be made to better fit the knee, ankle, leg, wrist, elbow, and arm, as discussed below. For example, as shown in FIG. 2B, another brace 250 could be formed with anterior half 251 formed to have a semicircular profile and the posterior half 252 formed with a trapezoidal profile to provide a better fit over the knee, elbow, etc. Further, any such braces could be made and sold in standard sizes, such as small, medium or large, or custom made to order. The advent of 3D printing to quickly and inexpensively form custom molds may facilitate production of custom braces.

Referring back to FIG. 2A, the annular brace 200 has a top ring 202 and a bottom ring 204, both formed as solid ribbons of material around the top and bottom of the structure, with one or more sections or side panels having different size holes, such as panels 210 and 220, formed between the top and bottom rings. The side panels may be uniform in material thickness and density, but preferably, the material will vary in thickness and/or density as a means to define support portions of the brace as discussed below. For example, the panels may be molded generally to a thickness of 2.5 mm, but additional material could be added to specific support portions. For example, panel 210 covers most of the area between the rings 202, 204, and may be molded with a standard thickness of 2.5 mm, while smaller panel 220 may be molded with an increased thickness of up to 5 mm to enhance the ability of the smaller panel 220 to both stabilize the underlying joint and to store energy for resistance to movement of the joint. Friction bumps 206 may be formed on the inside portion of the top ring 202 to help grip the body above the joint and keep the brace from slipping.

In this embodiment, side panel 210 has a pattern of large holes 212 formed throughout the panel. For example, the large holes 212 may be formed to have a diameter of 12.7 mm (½ inch). Side panel 220 covers a smaller, specifically targeted area of the brace, e.g., a vertical section between the rings 202, 204, and has a pattern of smaller holes 222 formed throughout that section, for example, with a diameter of 6.35 mm (¼ inch). By making the holes 222 smaller, the side panel 220 or support panel has more material disposed through that section than side panel 210 and can therefore provide more support through a range of motion of the underlying joint. Thus, the support panel 220 should be formed along a line or section of the brace that is coplanar with the plane of motion for the underling joint, on the anterior side of the joint. A circular section 230 having large holes 232 may be formed in the middle of the smaller hole section 220 as less restrictive area for the knee cap (patella) or the elbow, for example. More than one support panel may be formed in a brace to provide support along multiple planes of motion. Further, as noted above, an increased thickness of material may be used in regions having supports panels. Alternatively, or in addition, support panels may be formed along one or more meridians of the body.

Thus, in general, a flexible brace can be designed to control any the range of motion for any joint. The use of thinner and thicker portions of material in the brace, combined with the use of larger and smaller holes, can be engineered for particular physical issues to provide appropriate joint stabilization as well as energy storage to resist undesirable joint movements.

Although commercial processes are likely to create and use standard injection type molds, the emergence of 3D printing processes may allow a variety of molds to be easily and inexpensively built with amazing accuracy, in the shape of anything from a straight cylinder to a bent elbow. Software to create 3D objects is readily available, such as Adobe® Photoshop CS6 Extended software with 3D modeling option. Further, 3D printers are also readily available, such as the MakerBot Replicator 2 3D printer, or the FlashForge 3D printer. Such customization will enable the production of braces to control/stabilize any range of motion for any limbs/joints. Further, although 3D printing is still in its infancy, it is conceivable that it could be used to produce the actual braces rather than just the molds.

Creating an effective brace involves two steps. First, two fixed points are selected on the limbs to which the brace will be secured, then, material is formed between the two points so as to create a smooth surface against the skin. The volume of the material may be varied in different planes of movement. Any material in linear series will be fixed at the two points on the limb and stretched over the instantaneous axis of rotation for the joint, thus decelerating the effective moment arm that acts around the axis of rotation.

Because the two points are fixed, the flexible material will lengthen away from the joint center as the joint moves through a range of motion that changes the joint angle. At the joint rest or starting position, no tension is stored in the brace. However, at the end position, elastic energy will be stored in the brace.

The Poisson effect is an important mechanical characteristic that relates to the forces that are applied and created across a cross-section of material. Basically, when a body is subject to a uniaxial stress in one planar direction, a strain is created in the other two perpendicular planes that increases the dimension the material in those perpendicular planes. The converse is also true. For example, a body experiencing a tensile load which generates an increase in its axial dimensions also generates a decrease in its transverse dimensions. Thus, by having top and bottom rings secured at a fixed point relative to the joint, the brace will self-tighten onto the limb thereby helping to stabilize the underlying joint(s) and hold the brace in place on the surface of the skin, in combination with the use of friction bumps on the inside of the rings.

As the brace de-forms about the joint center, the moment arm of the joint is pushed out to the surface of the skin, thereby increasing the load applied to the brace. The change in the joint angle is proportional to the amount of tension stored in the brace, and as the joint flexes, more energy is stored in the brace. Further, due to the Poisson effect, the tension is passed laterally through the brace wall as well as circumferentially around the brace.

In general, any material that exists anterior to the joint center will decrease knee flexion, and any material located posterior to the joint center will decrease knee extension. Likewise, material located laterally to the knee will decrease varus loading, while material located medially to the knee will decrease valgus loading.

If the brace has a uniform consistency and thickness, the wall created against the skin makes it difficult to differentiate the volume of material and to vary loads in specific directions. However, by using holes in the material and varying the circumference of the holes, effective stabilization and support for the underlying can be created. Thus, the use of larger holes presents less elastic in series thereby creating less resistance. However, the use of smaller holes puts more elastic in series thereby creating more resistance in a given direction of movement. The ability to create a linear resistance in a specified direction applies to all three planes of movement and is essential to creating smooth and efficient movement patterns.

Increasing the volume of material in selected areas between the rings enables coordinating pressure over joint centers as they move through ranges of motion. Advantageous, the volume of material can be increased by forming "straps" of additional material on the surface of the brace in the direction the myofascial meridians. The straps are formed as part of the initial molding of the brace. As the joint goes through flexion and extension, tension is passed though the elastic matrix pulling on the straps to secure them as well as lengthening them across the instantaneous joint center, much like bending a beam.

The placing of more material in line with the myofascial meridians helps to secure the brace in place as well as help support and control the dynamic nature of the joint center and direct force over or in a plane of motion.

4. Support Brace for Knee

Figure 3A:
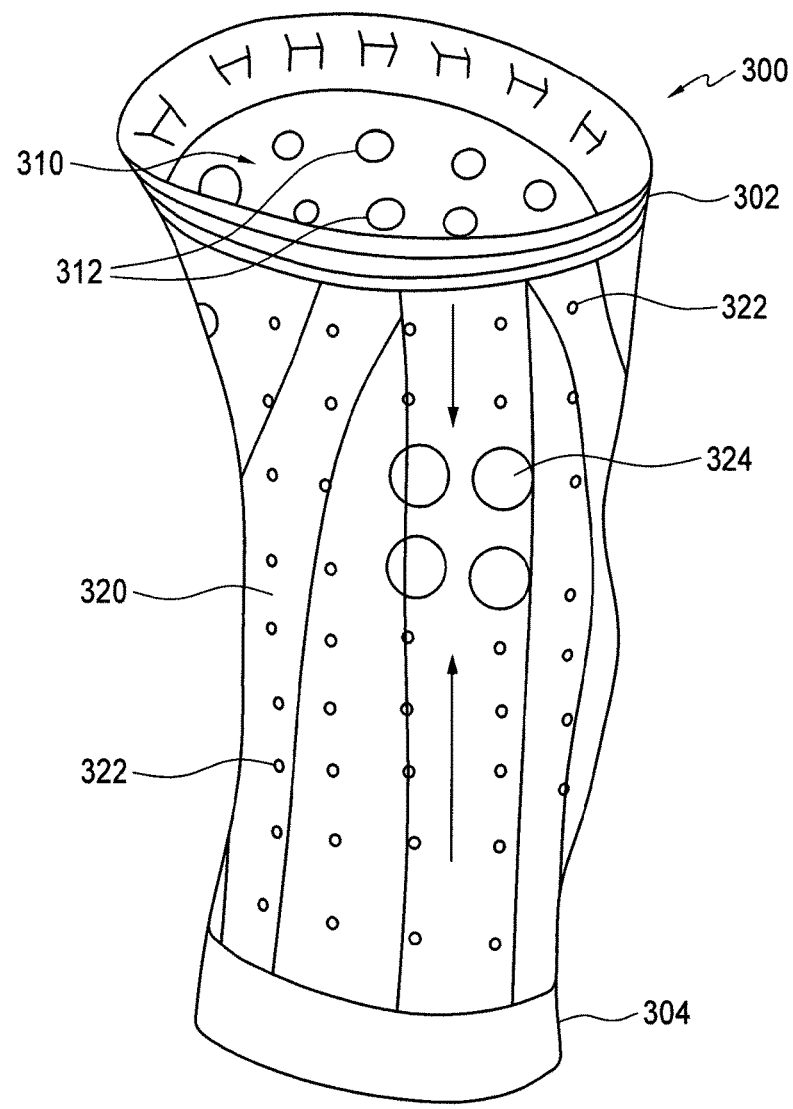
FIG. 3A is a front perspective view of a knee brace.

FIG. 3A illustrates a brace 300 formed to better fit and support the knee. For example, the top ring 302 and corresponding top portion of the brace may have a larger diameter to better fit above the knee, and a slight rearward tilt. The bottom ring 304 and corresponding bottom portion of the brace have a smaller diameter to better fit below the knee. The posterior portion 310 of the brace 300 has a pattern of large diameter holes 312, while the anterior portion 320 of the brace has a pattern of smaller diameter holes 322. Further, several larger holes 324 are formed in correspondence with the patella. Thus the smaller holes 322 provide a linear series resistance on the anterior side to flexion and extension movements of the knee joint.

Figure 3B:
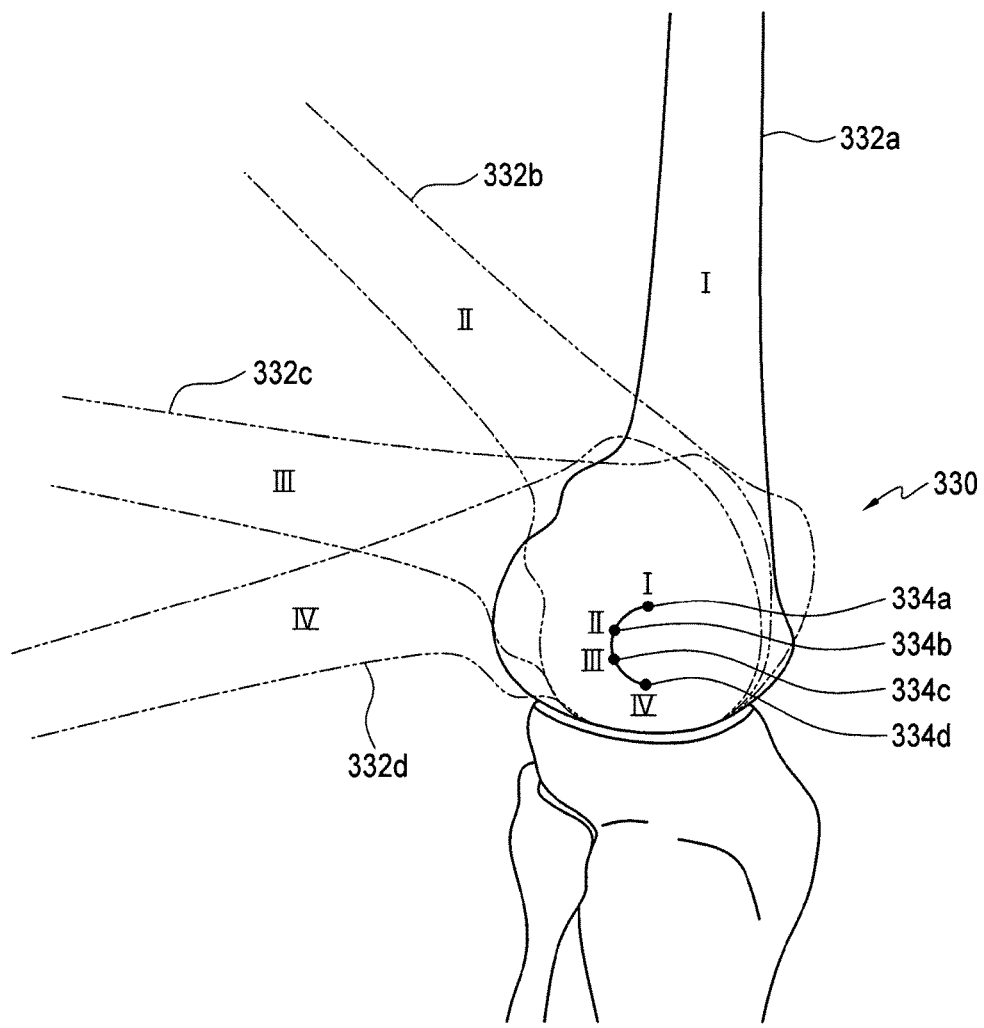
FIG. 3B is a front plan view illustrating a knee joint in four different rotational positions.

FIG. 3B illustrates the knee joint 330 with the femur 332 in four different positions. In position I (332a), the leg is straight with the knee in full extension. In position IV (332d), the leg is bent at the knee in full flexion. Position II (332b) and position III (332c) are intermediate positions. When building any brace, the center of rotation for the underlying joint is a key location. In some joints, however, like the knee, the center of joint rotation is not fixed in one spot, but moves with a flexion or extension movement. This movement is also illustrated in FIG. 3B, where point 334a is the instantaneous center of rotation when the knee is in position I; point 334b is the instantaneous center of rotation when the knee is in position II; point 334c is the instantaneous center of rotation when the knee is in position III; and point 334d is the instantaneous center of rotation when the knee is in position IV.

Figure 3C:
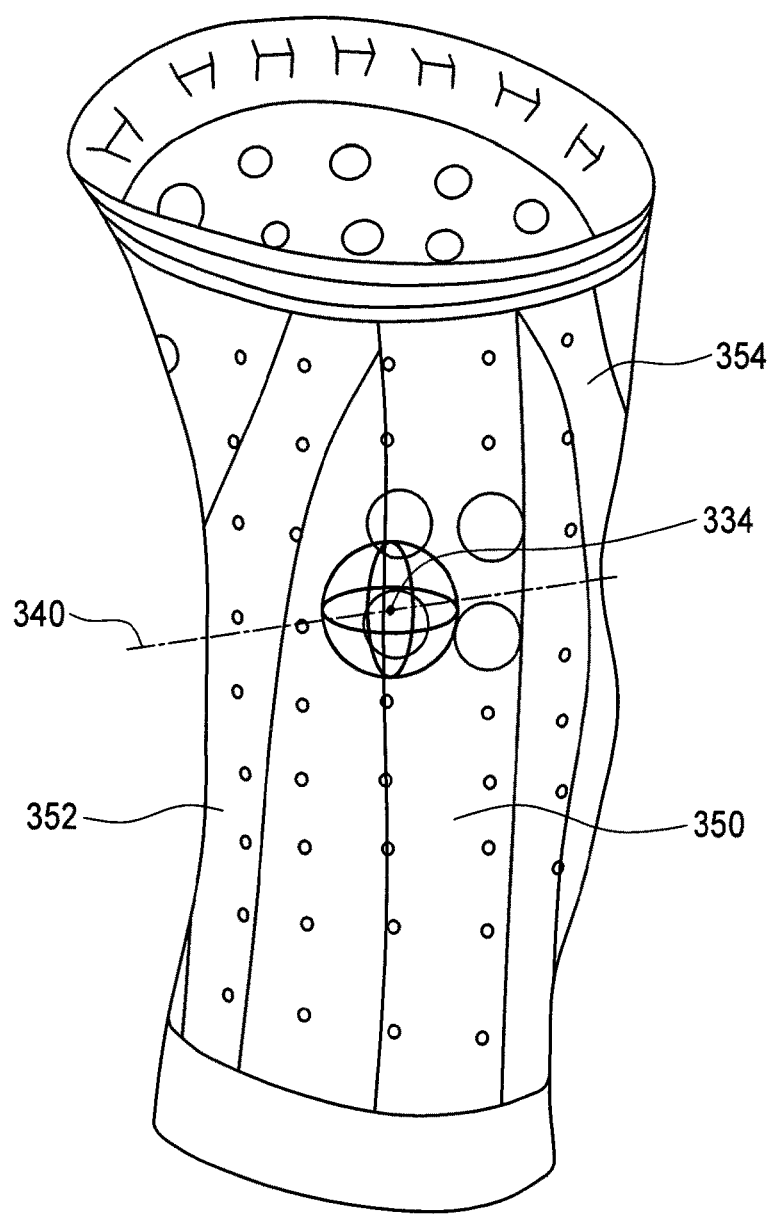
FIG. 3C is a front perspective view of the knee brace of FIG. 3A showing the axis of knee joint rotation.
Figure 3D:
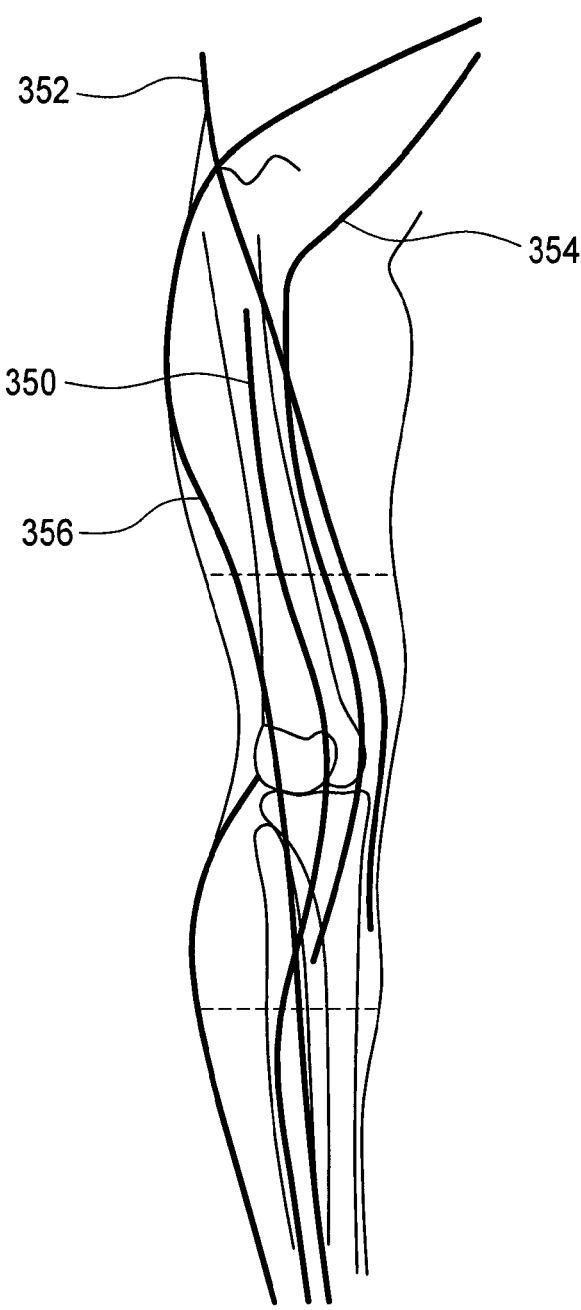
FIG. 3D is a front plan view of a human right leg showing the myofascial meridians running through the leg.

FIG. 3C is similar to FIG. 3A, but includes an axis of rotation 340 around the instantaneous center point 334 superimposed on the knee brace 300. Further, the relationship of significant meridian lines to the knee joint is also shown on FIG. 3C. For example, the superficial front line (SFL) 350 is behind the center of the brace on the anterior side; the lateral line (LL) 352 is behind the outside portion of the knee joint; and the deep front line (DFL) 354 is behind the inside portion of the knee joint. These meridians are also illustrated relative to the right knee in FIG. 3D.

Figure 3E:
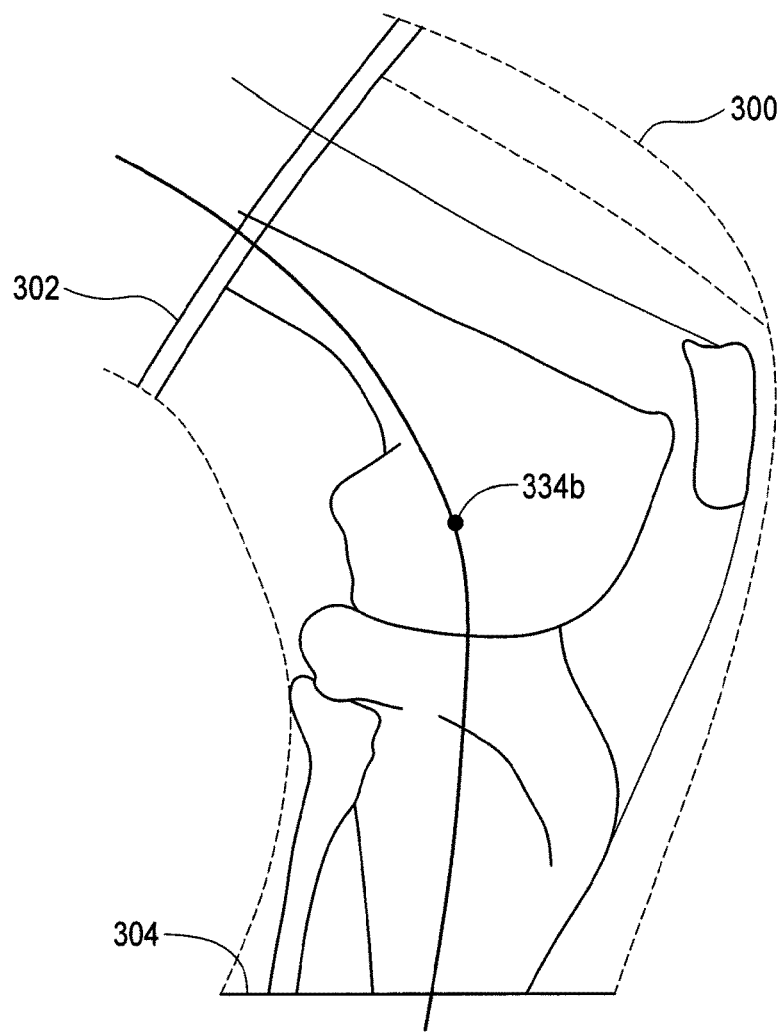
FIG. 3E is a front plan view illustrating the knee brace of FIG. 3A over the knee joint of FIG. 3B in one of the bent positions.

FIG. 3E shows the brace 300 covering the knee joint 330 in position II having center of rotation 334b, with top ring 302 snugly fit above the knee and bottom ring 304 snugly fit below the knee.

An evaluation of the performance of the knee brace was performed using a seated knee extension machine. A vertical stack of weights was loaded onto the machine, and the subject performed weighted leg extensions according to the standard control and test battery used by the National Strength and Conditioning Association (NSCA). For example, the tests started with high weight and low repetitions then moved to low weight and high repetitions.

Four different attributes were tested, namely, anaerobic power, anaerobic endurance, aerobic strength, and aerobic endurance. The trials included a 5 minute warm-up on an exercise bicycle with no brace; then a control battery with no brace; and finally a test battery with brace. The trials indicated that, while wearing the knee brace, an increase of approximately 35% in anaerobic power was observed; an increase of approximately 37% in anaerobic endurance was observed; an increase of approximately 38.5% in aerobic strength was observed; and an increase of approximately 25% in aerobic endurance was observed;

5. Support Brace for Ankle

Figure 4:
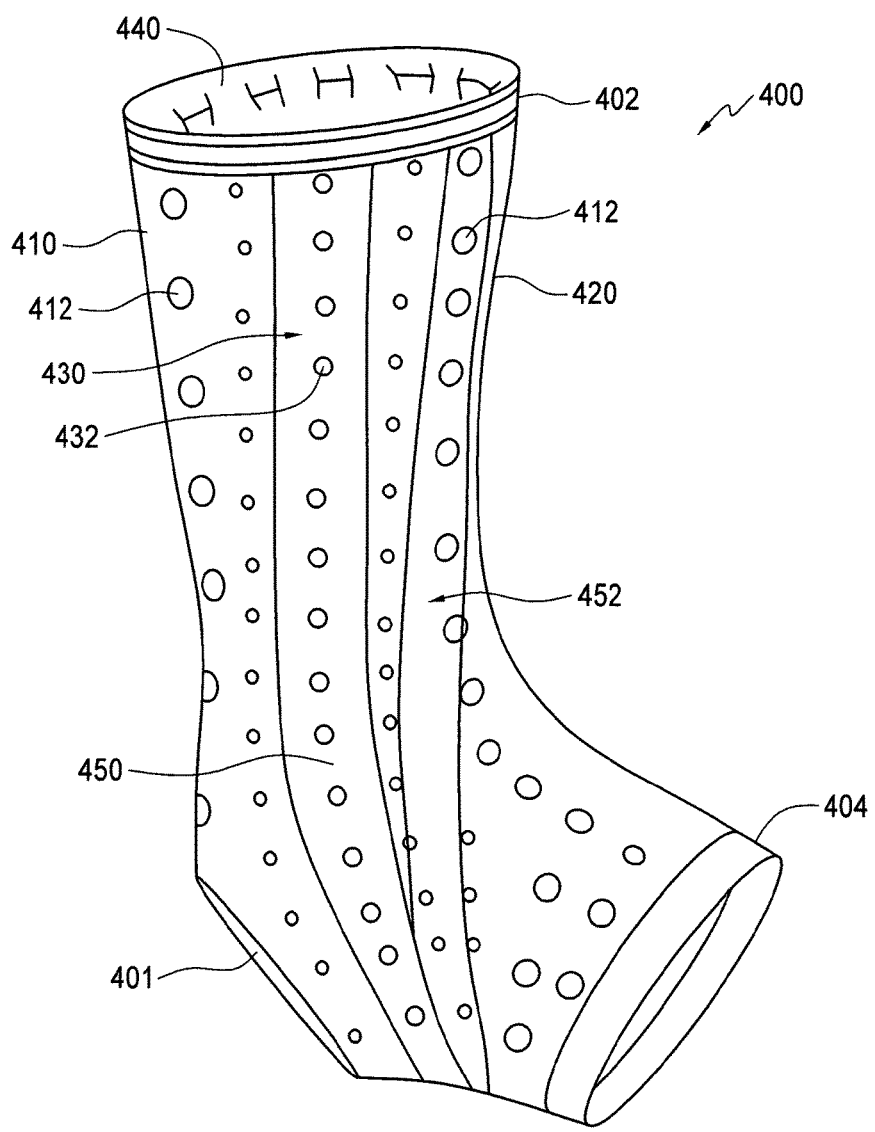
FIG. 4 is a front perspective view of an ankle brace.

FIG. 4 illustrates a brace 400 formed to better fit and support the ankle, the brace is formed in a L-shape between the top ring 402 and the bottom ring 404 to match the shape of the foot, with a heel opening 401. The top ring 402 is sized to fit snugly above the ankle, and the bottom ring 404 is sized to fit around the foot. The posterior portion 410 and the anterior portion 420 of the brace 400 have patterns of large diameter holes 412, while the inside portion 430 and outside portions 440 have patterns of smaller diameter holes 432. The smaller holes 432 are vertically oriented to follow the spiral line lateral meridians 450 on both the medial and lateral portions of the ankle, while the larger holes 412 are vertically oriented on the posterior side of the ankle and also vertically oriented to follow the superficial front line meridian 452 on the anterior side. The smaller holes 432 provide a linear series resistance on both the medial and lateral portions of the ankle to rotational movements of the ankle joint.

6. Support Brace for Wrist

Figure 5:
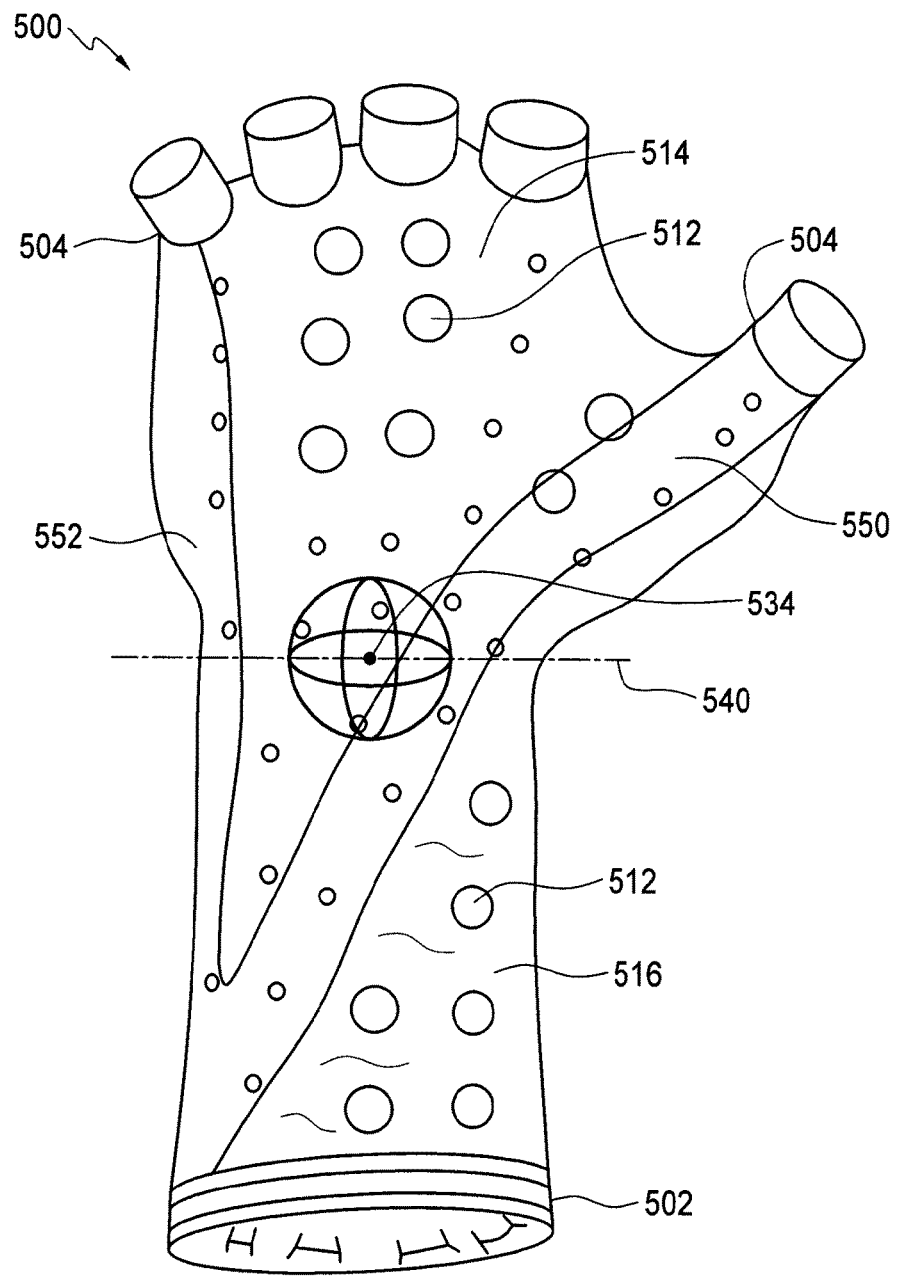
FIG. 5 is a front perspective view of a wrist brace.

FIG. 5 illustrates a brace 500 formed to better fit and support the wrist. The brace 500 is formed like a glove, with five ringed finger openings 504 at one end and a top ring 502 sized to fit snugly above the wrist. Patterns of large diameter holes 512 are formed through the palm area 514 and through the area 516 below the thumb. However, it may be desirable to have an open area of no material is the palm area to enable gripping a racket or club, or an area of less material for an injury such as carpal tunnel, which does not require restrictive pressure from the palm side. Area 516 below the thumb is a compressed zone because the hand pronates around axis 540 that runs through the joint center 534, and supinates in the resting position. Patterns of smaller holes 514 are oriented to follow the deep front arm line meridian 550 that runs from the outside of the wrist across to the end of thumb, and also to follow the deep back arm line 552 that runs along the outside of the hand. The smaller holes 514 provide a linear series resistance on both the inside and outside of the wrist to rotational movements of the wrist joint.

7. Support Brace for Elbow

Figure 6:
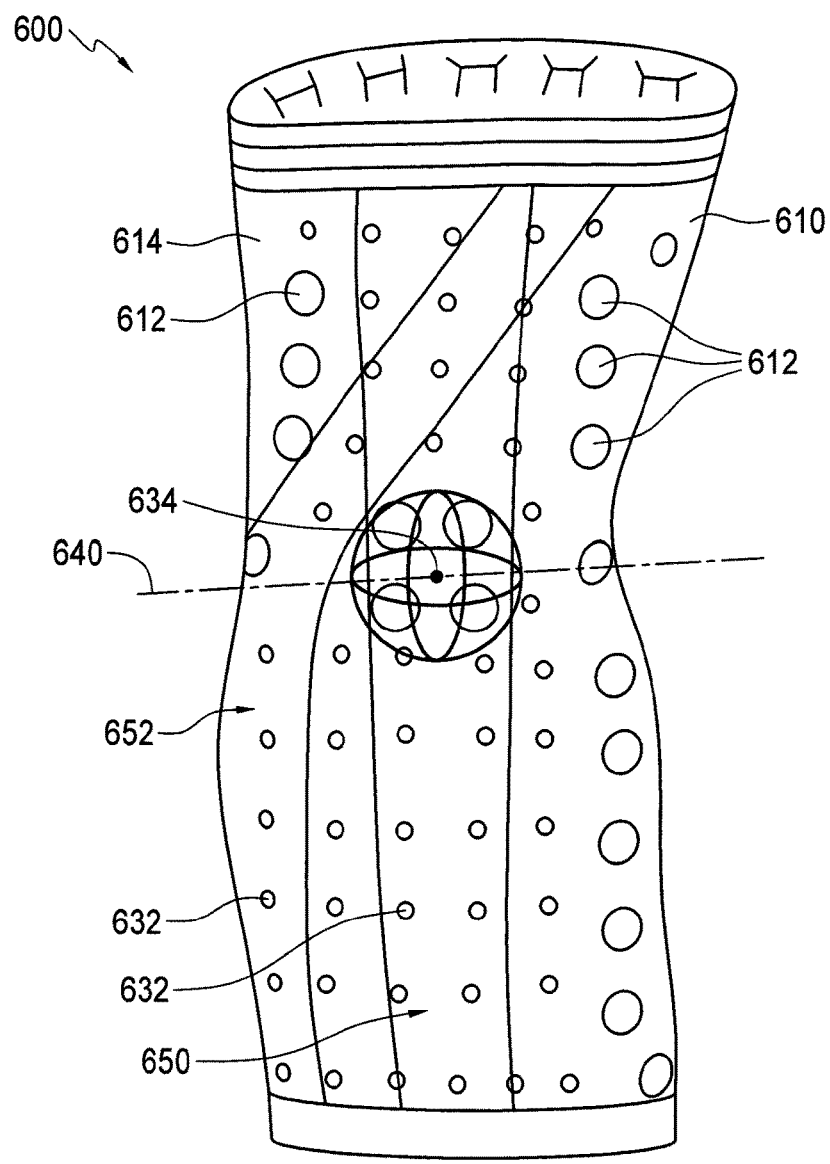
FIG. 6 is a rear perspective view of an elbow brace.

FIG. 6 illustrates a brace 600 formed to better fit and support the elbow. The brace 600 is formed much like the knee brace 300, with a top ring 602 sized to fit snugly above the elbow and a bottom ring 604 sized to fit snugly below the elbow. Patterns of large diameter holes 612 are formed vertically along the entire length of the anterior section 610 and also in the posterior section 614 above the elbow. Patterns of smaller holes 632 are oriented to follow the superficial back arm line meridian 650 that runs straight through the elbow, and also to follow the deep back arm line meridian 652 that runs from the outside of the elbow on the anterior side across to the inside of the elbow on the posterior side. The smaller holes 632 provide a linear series resistance to rotational movements of the elbow joint.

8. Conclusion

While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. A knee brace, comprising:
   an annular structure formed of flexible elastic material to conform to a human knee, the annular structure having a posterior section and an anterior section, the anterior section configured to conform to an anterior region of the human knee and cover a knee joint and formed with an increased volume of the flexible elastic material relative to the posterior section, the posterior section configured to conform to a posterior region of the human knee.

2. The knee brace of claim 1, the anterior section further comprising a first lateral section formed at a first edge of the anterior section and configured to conform to a first lateral region extending around an outside anterior portion of the knee joint.

3. The knee brace of claim 2, wherein the posterior section is formed to have a first plurality of holes having a first size, the anterior section is formed to have a second plurality of holes having a second size, and the first lateral section is formed to have a third plurality of holes having the second size, wherein the second size is smaller than the first size in order to provide the increased volume of flexible elastic material relative to the posterior section.

4. The knee brace of claim 1, wherein the posterior section is formed to have a first plurality of holes having a first size, and the anterior section is formed to have a second plurality of holes having a second size, wherein the second size is smaller than the first size in order to provide the increased volume of flexible elastic material relative to the posterior section.

5. The knee brace of claim 4, wherein the first and second plurality of holes are circular, and the second size is a smaller diameter than the first size.

6. The knee brace of claim 1, the annular structure further comprising:
a top circular ring configured to be secured above the knee; and
a bottom circular ring configured to be secured below the knee;
wherein the posterior section and the anterior section are secured in a vertical orientation between the top ring and the bottom ring, the posterior section formed with a first plurality of holes having a first size, and the anterior section formed with a second plurality of holes having a second size, wherein the second size is smaller than the first size thereby providing the increased volume of flexible elastic material relative to the posterior section.

7. The knee brace of claim 6, the anterior section further comprising:
a first lateral section formed at a first edge of the anterior section to have a third plurality of holes having the second size, the first lateral section secured in a vertical orientation between the top ring and the bottom ring and configured to conform to a first lateral region extending around an outside anterior portion of the knee joint.

8. The knee brace of claim 7, the anterior section further comprising:
a second lateral section formed at a second edge opposite the first edge of the anterior section to have a fourth plurality of holes having the second size, the second lateral section secured in a vertical orientation between the top ring and the bottom ring and configured to conform to a seconds lateral region extending around an inside anterior portion of the knee joint.

9. The knee brace of claim 1, the anterior section further comprising a second lateral section formed at a second edge opposite the first edge of the anterior section and configured to conform to a second lateral region extending around an inside anterior portion of the knee joint.

10. A knee brace, comprising:
an annular structure formed of flexible elastic material to substantially conform to a human knee, the annular structure having a posterior section and an anterior section, the anterior section configured to conform to an anterior region of the human knee and cover a knee joint, the posterior section formed with a first plurality of holes having a first size, and the anterior section formed with a second plurality of holes having a second size, wherein the second size is smaller than the first size thereby providing an increased volume of the flexible elastic material in the anterior section relative to the posterior section.

11. The brace of claim 10, the anterior section further comprising:
a first lateral section formed at a first edge of the anterior section to have a third plurality of holes having the second size, the first lateral section configured to conform to a first lateral region extending around an outside anterior portion of the knee joint.

12. The knee brace of claim 10, the anterior section further comprising a second lateral section formed at a second edge opposite the first edge of the anterior section and configured to conform to a second lateral region extending around an inside anterior portion of the knee joint.

13. A knee brace, comprising:
a first ring configured to be secured above a knee joint of a human knee;
a second ring configured to be secured below the knee joint;
a posterior panel secured between the first ring and the second ring, the posterior panel is formed to have a first volume of flexible elastic material and is configured to conform to a posterior region of the human knee; and
an anterior panel secured between the first ring and the second ring, the anterior panel is formed to have a second volume of flexible elastic material, the second volume is greater than the first volume, and is configured to conform to a posterior region of the human knee.

* * * * *